Nov. 8, 1938. D. AICARDI Plant Pat. 304
ROSE
Filed Aug. 10, 1937
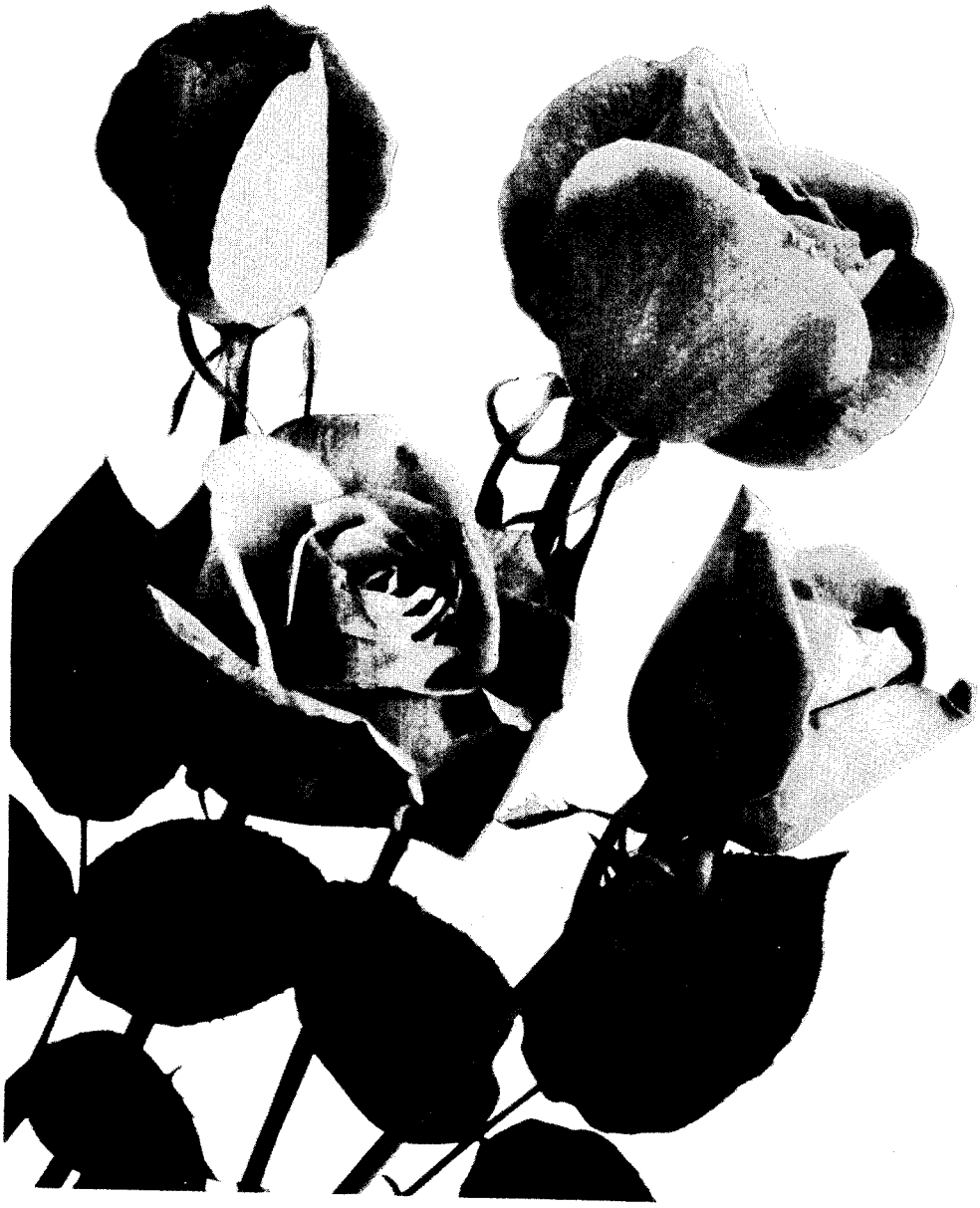
Inventor
D Aicardi
By Robb & Robb
Attorneys Patented Nov. 8, 1938

UNITED STATES PATENT OFFICE

304

ROSE

Domenico Aicardi, San Remo, Italy, assignor to
Jackson & Perkins Company, Newark, N. Y.

Application August 10, 1937, Serial No. 158,413

1 Claim. (Cl. 47—61)

The present invention relates to improvements in rose plants having for its object the production of a variety of red color with large size, hardiness and vigor as its dominating characteristics.

In the origination of this new variety, I had particularly in mind the demand of both the cut rose trade and nurserymen for a red Dame Edith Helen and, therefore, selected this variety for crossing with the well known variety Sensation. From crosses of Dame Edith Helen and Sensation, and reciprocally Sensation and Dame Edith Helen, several thousand seedlings were raised.

The present rose was selected from these seedlings after several years of testing both in Italy and America. In the course of these tests, it has been budded on various stocks, such as Odorata, Manetti, and Multiflora, and I have found it to come uniformly true.

This new variety is especially characterized by its unusual vigor, hard wood, and superior winter hardiness, as has been particularly proven by the tests in America where plants grown in test gardens in northern New York have suffered no injury for two winters in succession.

The flower is noted for its very large size such as characterized the early Hybrid Perpetuals, its red color so much desired being substantially unaffected by age or weather.

The tests aforesaid have included growing as a cut flower variety, and its steady production is found highly satisfactory.

The following is a detail description of the new variety, reference therein to color according with the Gravereaux color standard, except where obviously the ordinary dictionary definition is meant:—

Parentage:
- *Seed parent.*—Dame Edith Helen.
- *Pollen parent.*—Sensation.

Classification:
- *Botanic and commercial.*—Hybrid Tea.

*Flower*

Blooming habit:
- Observations made daily for two seasons in Jackson & Perkins nurseries and greenhouses.
- Recurrent—Continuous.

Bud:
- *Size.*—Very large.
- *Form.*—Ovoid, unaffected by wet or hot weather.
- *Color.*—When sepals first divide—blood red. When petals begin to unfurl—cerise. When half blown: inside of petals—vermilion; reverse of petals—cerise.
- *Sepals.*—Smooth edge, branched, "hood" above bud. Curl back when bud unfurls.
- *Calyx.*—Shape—funnel. Size—large. Aspect—smooth. Color—medium green. Strength—erect, heavy.
- *Opening*—Opens well. Is not affected by adverse conditions.

Bloom:
- *Size.*—Very large. Average size when fully expanded 4 to 5″.
- *Borne.*—Singly.
- *Stems.*—Long, strong.
- *Form.*—Globular. Retains its form to the end.
- *Petalage.*—Very double. Number of petals under normal conditions—50 to 60.
- *Color.*—Center of flower—vermilion. Outer petals—blood red. Base of petals—blood red. Inside of petals—vermilion. Reverse of petals—cerise. General tonality from a distance—vermilion.
- *Variegations.*—None.
- *Discoloration.*—No discoloration first and second days. Third day—slight paling in center.

Petals:
- *Texture.*—Thick. Unaffected by wet or hot weather.
- *Appearance.*—Inside—velvety. Outside—satiny.
- *Form.*—Round.
- *Arrangement.*—Imbricated (regularly arranged shinglelike). Petaloids in center—few, large.
- *Persistence.*—Hang on and dry.
- *Fragrance.*—Strong. Nature—"Old Rose perfume" (Centifolia).
- *Lasting quality.*—On the plant and as cut flower, very long.

Genital organs:
- *Stamens, anthers.*—Large, few. Color—yellow. Arrangement—mixed with with petaloids.
- *Stamens, filaments (threads).*—Medium. Color—yellow.
- *Pollen.*—Lemon yellow.
- *Styles.*—Loosely separated. Uneven length, medium length, heavy.
- *Stigmas.*—White.
- *Ovaries.*—Some protruding from calyx.

Fruit:
- Variety is rarely fertile with its own pollen.
- *Form.*—Ovoid, round headed.
- *Aspect.*—Smooth.
- *Color at maturity.*—Scarlet.
- *Sepals.*—Caducous (soon falling).

*Plant*

Form:
- Bush.

Growth:
- Very vigorous, upright.

Foliage:

Generally five leaflets.

*Size.*—Very large.

*Quantity.*—Abundant.

*Color.*—New foliage—dark green. Old foliage: upper side—dark green; under side—lighter green.

*Shape.*—Oval pointed.

*Texture.*—Upper side—leathery. Under side—smooth. Ribs and veins—ordinary.

*Edge.*—Serrated (saw toothed).

*Serration.*—Single, small.

*Rachis.*—Color—green. Under side—smooth.

*Stipules.*—medium, smooth.

*Disease resistance.*—Susceptible to mildew.

Wood:

*New wood.*—Color—light green. Bark—smooth.

*Old wood.*—Color—green. Bark—smooth.

Thorns (divided into thorns, prickles and short needles):

*Thorns.*—Quantity: on main stalks from base—ordinary; on laterals from stalk—few. Form—broad base, medium, hooked downward. Color when young—red. Position—irregular.

*Prickles.*—Quantity—none.

*Short needles.*—Quantity—none.

I claim:

A new and distinct variety of Hybrid Tea rose plant, characterized by its great vigor and hardiness for outdoor use, the large size and vermilion color of its flowers, and its particular adaptability for under glass culture for the cut rose market, substantially as shown and described.

DOMENICO AICARDI.